(12) United States Patent
Flynn et al.

(10) Patent No.: US 10,429,277 B2
(45) Date of Patent: Oct. 1, 2019

(54) MAGNETIC NEEDLE SEPARATION AND OPTICAL MONITORING

(71) Applicant: Imagion Biosystems Inc., Albuquerque, NM (US)

(72) Inventors: Edward R Flynn, Peiora, AZ (US); Erika Vreeland, Albuquerque, NM (US)

(73) Assignee: Imagion Biosystems, Inc., San Diego, CA (US)

( * ) Notice: Subject to any disclaimer, the term of this patent is extended or adjusted under 35 U.S.C. 154(b) by 0 days.

(21) Appl. No.: 15/937,705

(22) Filed: Mar. 27, 2018

(65) Prior Publication Data

US 2018/0231437 A1 Aug. 16, 2018

Related U.S. Application Data

(63) Continuation of application No. 14/679,216, filed on Apr. 6, 2015, now Pat. No. 9,964,469.

(51) Int. Cl.
| | |
|---|---|
| *G01N 1/04* | (2006.01) |
| *B03C 1/28* | (2006.01) |
| *G01N 21/59* | (2006.01) |
| *G01N 33/543* | (2006.01) |
| *A61B 10/02* | (2006.01) |
| *A61B 90/00* | (2016.01) |
| *A61B 17/00* | (2006.01) |

(52) U.S. Cl.
CPC ............ *G01N 1/04* (2013.01); *A61B 10/0233* (2013.01); *A61B 90/39* (2016.02); *B03C 1/28* (2013.01); *G01N 21/59* (2013.01); *G01N 33/54326* (2013.01); *A61B 2017/00876* (2013.01); *A61B 2090/3908* (2016.02); *A61B 2090/3954* (2016.02); *B03C 2201/18* (2013.01); *G01N 2201/02* (2013.01); *G01N 2201/061* (2013.01)

(58) Field of Classification Search
CPC ...................................................... G01N 1/04
See application file for complete search history.

*Primary Examiner* — Scott Long
(74) *Attorney, Agent, or Firm* — V. Gerald Grafe (57) ABSTRACT

Apparatuses and methods for removing magnetic particles from suspensions are described. One embodiment of the apparatus is called a magnetic needle.

15 Claims, 9 Drawing Sheets

MAGNETIC NEEDLE SEPARATION AND OPTICAL MONITORING

CROSS-REFERENCE TO RELATED APPLICATIONS

This application is a continuation of application Ser. No. 14/679,216, filed Apr. 6, 2015, which is incorporated herein by reference.

BACKGROUND OF THE INVENTION

Field of the Invention (Technical Field)

The present invention relates generally to methods and apparatus for purifying or concentrating samples using magnetism.

Magnetic particle suspensions have been proposed for use in chemical and biological assays as well as biomedical research and clinical applications. For these applications, it can be important that the suspensions be free of excess reagents used in their synthesis or reactions that introduce surface functionality using polymers, biological molecules, etc. Residual impurities in the suspension following a reaction can alter the reactivity of the nanoparticles in downstream applications and can induce toxic side effects in biological samples. Typical particle separation methods include ultracentrifugation, column chromatography, dialysis, etc. These methods require either the use of expensive equipment or a large quantity of consumable materials and reagents.

SUMMARY OF THE INVENTION

The use of a magnetic needle as described herein to collect magnetic particles from a non-magnetic solution can provide a straightforward, cost-effective approach to separation. The properties of the magnetic needle scale with size, so that the construction of the needle can be varied to accommodate reactions of different volumes with maximum efficiency. The collected nanoparticles can be removed from the dispersant and resuspended in the medium of choice at the desired concentration. By monitoring the separation optically, the duration of the separation, the separation efficiency, and the quality of the suspension can also be assessed.

An example embodiment of the present invention provides an apparatus comprising a rod having a distal end and a proximal end with one or more rare-earth magnets located at the distal end of the rod, the rod capable of being inserted into and retracted an environment containing magnetic particles. The apparatus further includes a sheath that is removably attached to the rod and covers at least a portion of the rod that extends into the environment.

While the apparatus is in the environment, the magnetic particles are magnetically collected against the sheath of the rod over a period of time. The apparatus is separated from the environment with the particles magnetically attached to the sheath. The sheath having the magnetic particles attached thereto is removed from the rod. Removal of the sheath from the rod removes the magnetic attraction that attracted the particles to the apparatus, and the particles can then be separated form the sheath if desired, for example by washing the sheath.

In an example application, the magnetic collection time ranges from about 30 seconds to about 240 seconds.

BRIEF DESCRIPTION OF THE SEVERAL VIEWS OF THE DRAWINGS

FIG. 2 illustrates three views (FIG. 2a, FIG. 2b, and FIG. 2C) of three magnetic separation devices according to different embodiments of the present invention.

DETAILED DESCRIPTION OF THE INVENTION

As used herein "a" and "an" means one or more.

According to an example embodiment of the present invention, a magnetic apparatus assembly is provided, similar to a conventional needle with a central shaft and a thin-walled cylindrical channel surrounding the shaft.

Magnetic fields of an example embodiment of the present invention produce force fields to attract magnetic particles.

Superparamagnetic nanoparticles have the property that, if no magnetic field is present, (a field smaller or comparable to the earth's field), the particles behave paramagnetically, i.e. they have a permeability close to one. However, in a relatively strong magnetic field, they become aligned with that field and exhibit ferromagnetism with permeabilities of several thousand, depending on the particle properties and the strength of the applied magnetic field. This very unusual property means that they can be injected into a volume when there is no applied field without congealing through their own magnetic attraction, but will be strongly attracted to regions of a large applied field. Other bio-materials in the area that are paramagnetic are not affected.

Figure 1:
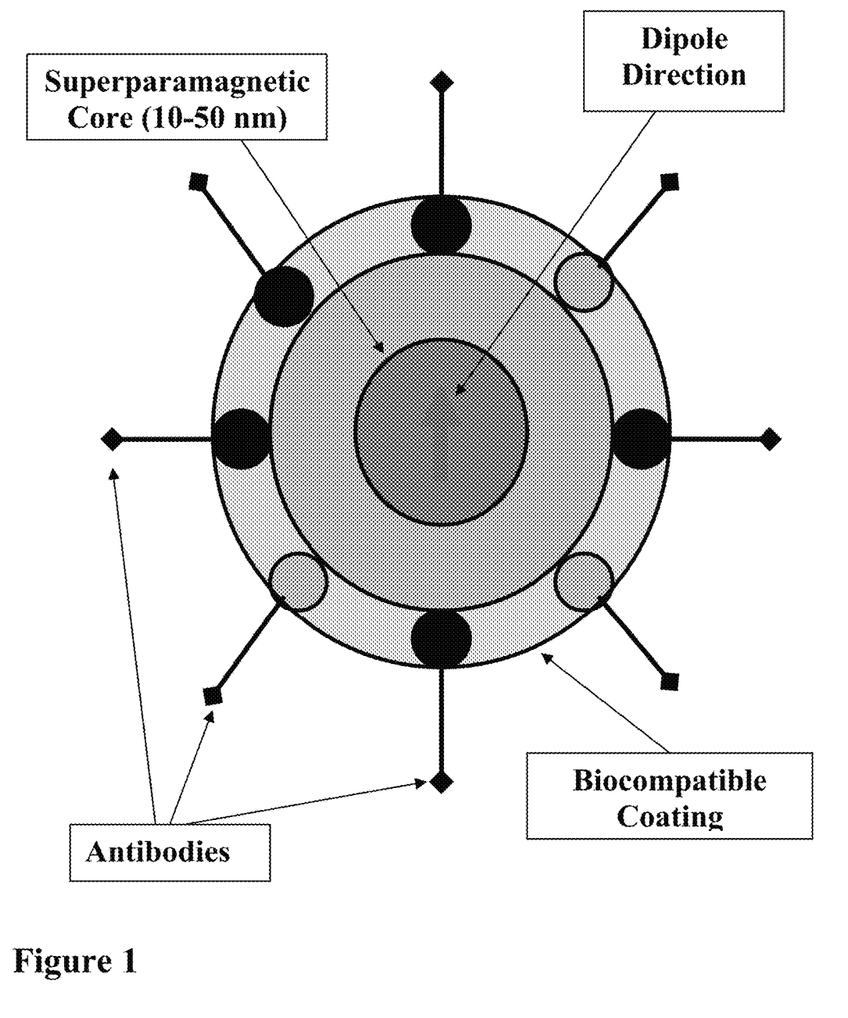
FIG. 1 is a graphical illustration of a magnetic nanoparticle which contains a ferrite core, a coating of a biocompatible material, and a coating of specific antibodies according to one embodiment of the present invention.

Referring now to FIG. 1, the concept of a magnetic nanoparticle coated with an antibody is illustrated according to one embodiment of the present invention. Superparamagnetism considerably enhances the collection, using embodiments of the present invention, of cells that have been coated with particles such as those in FIG. 1. According to one embodiment of the present invention, a antibody-labeled nanoparticles are introduced to a sample containing cells to which the antibodies can bind. After waiting for a specified period, a magnetically tipped rod producing a strong magnetic field is inserted into the sample and left for a predetermined collection time. The rod (also known as a wire) is removed with the cells containing the magnetic nanoparticles attached thereto. The nanoparticles are collected from the tip of the wire by either a strong magnetic field on the tip, or other mechanisms as described below.

Figures 2A, 2B, 2C:
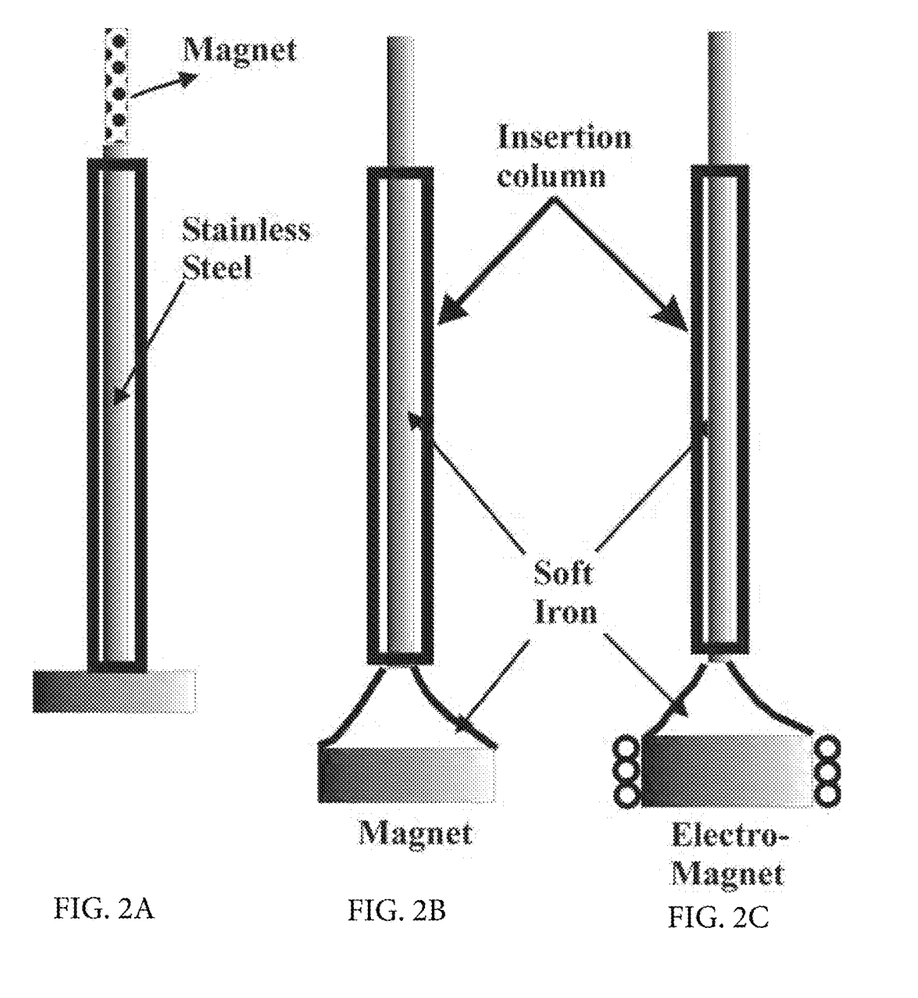
FIG. 2a illustrates a magnetic biopsy device comprising a guidance tube with a central needle containing a stainless steel rod and a magnetic tip on the end of the rod wherein the magnetic tip ranges in size from one (1) cm to five (5) cm in length according to one embodiment of the present invention.
FIG. 2b is a schematic illustration of an example magnetic biopsy device comprising a guidance tube with a ferrous needle attached at one end to a strongly magnetized material according to one embodiment of the present invention.
FIG. 2c is a schematic illustration of an example magnetic biopsy device comprising a guidance tube with a ferrous material attached at one end in addition to a strong electromagnet attached thereto according to one embodiment of the present invention.

Referring now to FIG. 2a, a tip of magnetic material of about 1 cm is located at one end of the central removable rod is illustrated according to another embodiment of the present invention. According to this configuration, magnetic material is located at the end of the rod at about the last cm of the central rod length. Magnetic material such as iron, or rare earth materials such as Knife, Smock, Ceramic, and Alnico can be used in these magnetic rods. Magnetic field intensity maximums can be about 4000 G for Ceramic 5 and about 13,000 G for Knife-42H with particular values of about 4000 G at the surface of the Knife magnets. The magnetic needle tip is of about one (1) mm diameter and about ten (10) mm length. The magnetic material can be located at any position along the length of the rod. The dimension of the magnetic needle can range in diameter from about 0.5 mm to about 10 mm. The dimension of the magnetic needle can range in length from about 1 mm to about 1000 mm.

Referring now to FIG. 2b, a magnetic needle with a removable magnet is illustrated according to an example embodiment of the present invention. This permits easy removal of the attached nanoparticles from the needle after extraction. In this embodiment, the needle is conically enlarged as it extends beyond the housing of a tube wall or canula and proceeds outside and becomes physically in contact with a larger magnet. This structure permits a concentration of magnetic lines from the magnet located at one end of the rod along the length of the rod to the small tip at the opposing end.

The material and geometry concentrate significant flux to the tip. A rare earth magnet is attached to the large end so that its magnetic flux lines will proceed through the needle and are emitted at the tip end. In this example embodiment of the present invention, large rare earth magnets can be used at the end of the rod that is opposite the insertion point, which is not inserted into the sample. The external magnet can be removed when the needle is extracted. In the absence of the magnetic field, the nanoparticles are removed from the needle by an additional external magnet extraction.

Referring now to FIG. 2c, an electromagnetic needle is illustrated according to an example embodiment of the present invention. In this example embodiment an electromagnetic coil wound around a ferromagnetic core and located at the end of the inserted magnetic needle produces the magnetic field. The external magnet field can be turned off when the needle is extracted to remove the nanoparticles from the needle by an additional external magnet extraction.

According to an example embodiment of the present invention, the compatibility of the needle (also known as a wire or rod) that is magnetizable is considered to avoid contact of rare earth magnetic material with the sample. The needle material can be coated with a thin plastic coating that is compatible with the sample. This coating also permits sterilization procedures and potential reuse of the needle.

In another embodiment of the present invention, an external magnet can be used to magnetize the magnetizable rod. The external magnet is used to increase the magnetic force on the particles in the vicinity of the needle. The external magnetic pole can be either permanently magnetized or electromagnetically excited. This magnetic circuit decreases the particle collection time at the needle. A rare earth or electromagnetic magnet is placed on the opposite side of the collection location to increase the magnetic divergence vector field at the needle location resulting in increase efficiency in collecting magnetic particles. According to an example embodiment of the present invention, the external magnet is similar to a commonly used C-magnet where in this case the C surrounds the collection volume and the needle is attached to one of the C-magnet faces. A Knife magnet, or alternatively an electromagnetic coil giving field strength of about 0.6 T, can be used to generate the magnetic field.

Figure 3:
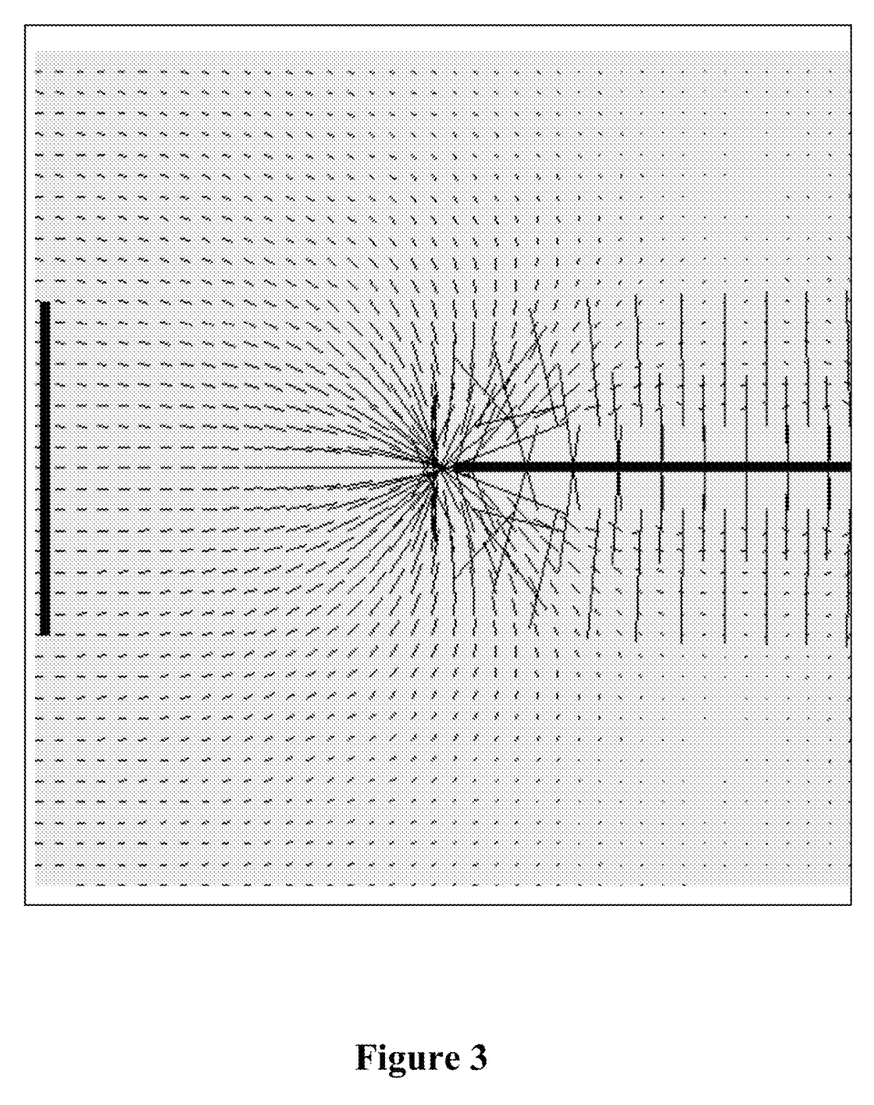
FIG. 3 is a schematic illustration of a calculation showing the magnetic fields in the vicinity of the magnetic needle.

FIG. 3 illustrates a magnetic field and the field derivatives of the magnetized needle extending to reasonable distances with the magnetizing fields from these magnets according to an example embodiment of the present invention. Magnetic field strength from the needle versus distance from needle in a two (2) cm by two (2) cm box.

Figure 4:
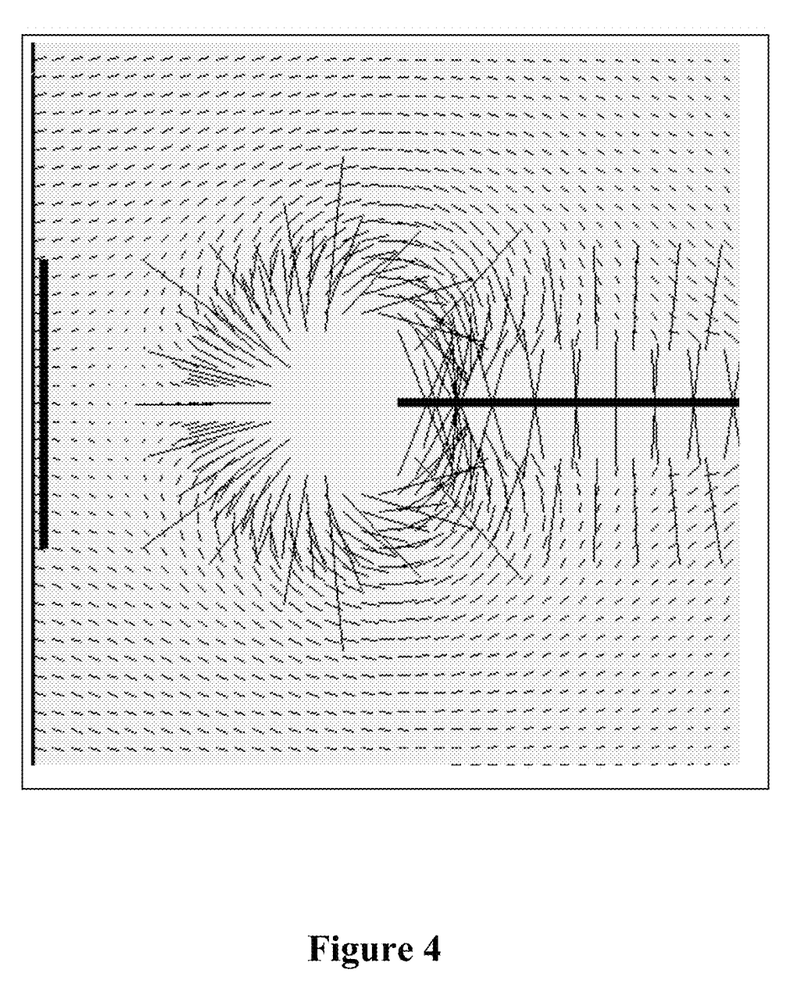
FIG. 4 is a schematic illustration of a calculation showing the force fields on magnetic nanoparticles in the vicinity of the magnetic needle.

Referring now to FIG. 4, the forces exerted on magnetic nanoparticles can be calculated using electromagnetic theory. Assuming that the viscosity of the medium is close to water and using Stokes theorem, it is possible to calculate the effective range of attraction and the time to pull nanoparticles to the needle. Magnetic lines of force on magnetic nanoparticles from the magnetic needle in a two (2) cm by two (2) cm box.

Figure 5:
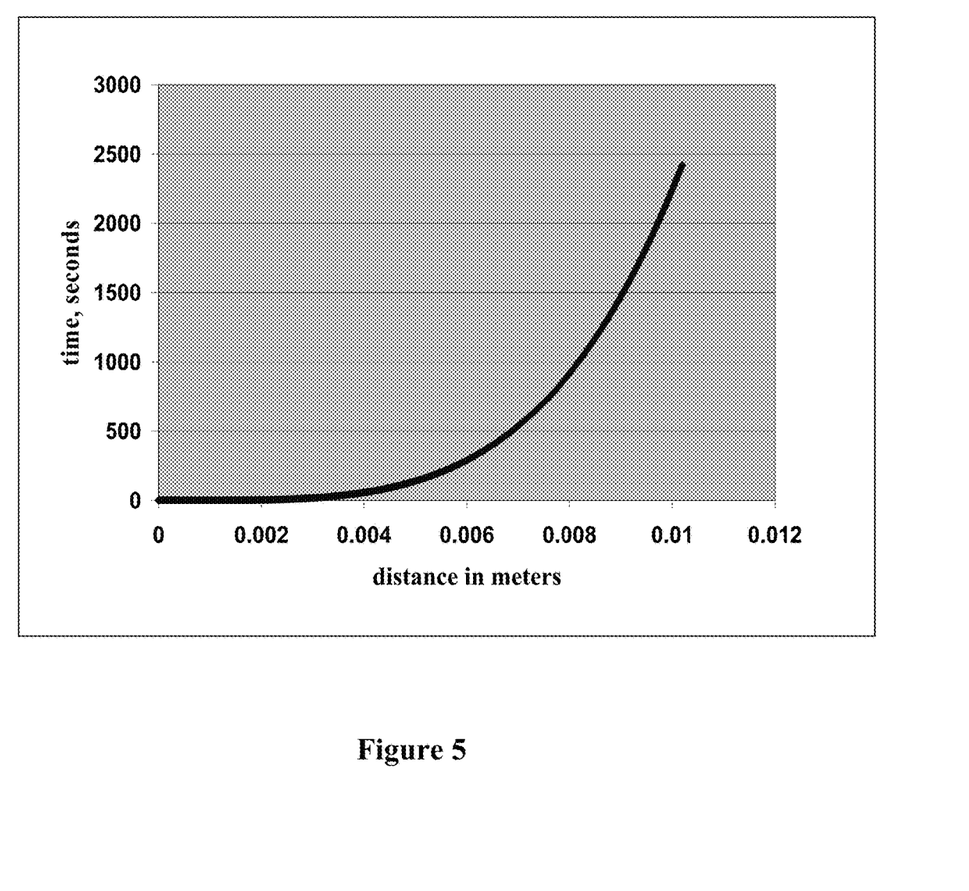
FIG. 5 is a schematic illustration of the results of a calculation showing the time it takes to pull magnetic nanoparticles onto a magnetic biopsy device as a function of the magnetic nanoparticles initial distance from the needle when the biopsy device is inserted into the environment.

Referring now to FIG. 5, detailed calculations of the forces, ranges, and collection times for various field strengths, needle configurations, and magnetic nanoparticles properties are illustrated in the graph. The time required to pull cells labeled with nanoparticles to the needle to provide the necessary guidance for collection times of the superparamagnetic particles are calculated according to an example embodiment of the present invention.

Large number of magnetic nanoparticles attach to each cell through the antibody mechanism and this adds considerably to the ability to attract the cells to the needle. For example, values of $2 \times 10^7$ nanoparticles per cell or 30 PG of superparamagnetic iron per cell are achievable. The range of the magnetic needle for attracting magnetic nanoparticles is calculated by modeling the magnetic needle used to collect the cells containing the nanoparticles as a magnetic dipole of dipole moment $\vec{m}$.

In an example application, human cancer or other cells are obtained from bone marrow biopsies from clinical examinations of patients suspected of bone marrow disease or metastasis. Magnetically-labeled antibodies directed against CD34 (leukemia cells and myelodysplasia marker) and cytokeratin (breast cancer marker) are one example of nanoparticles utilized. The level of normal cells expressing cytokeratin in normal bone marrow is negligible, and the level of normal cells expressing CD34 is significantly below 1% in normal marrows. Since tumor involves levels upwards of 100% of the marrow, these markers will detect and sample tumor cells preferentially, if the tumor is present. This significantly increases the specificity of the bone marrow biopsy.

Figure 6:
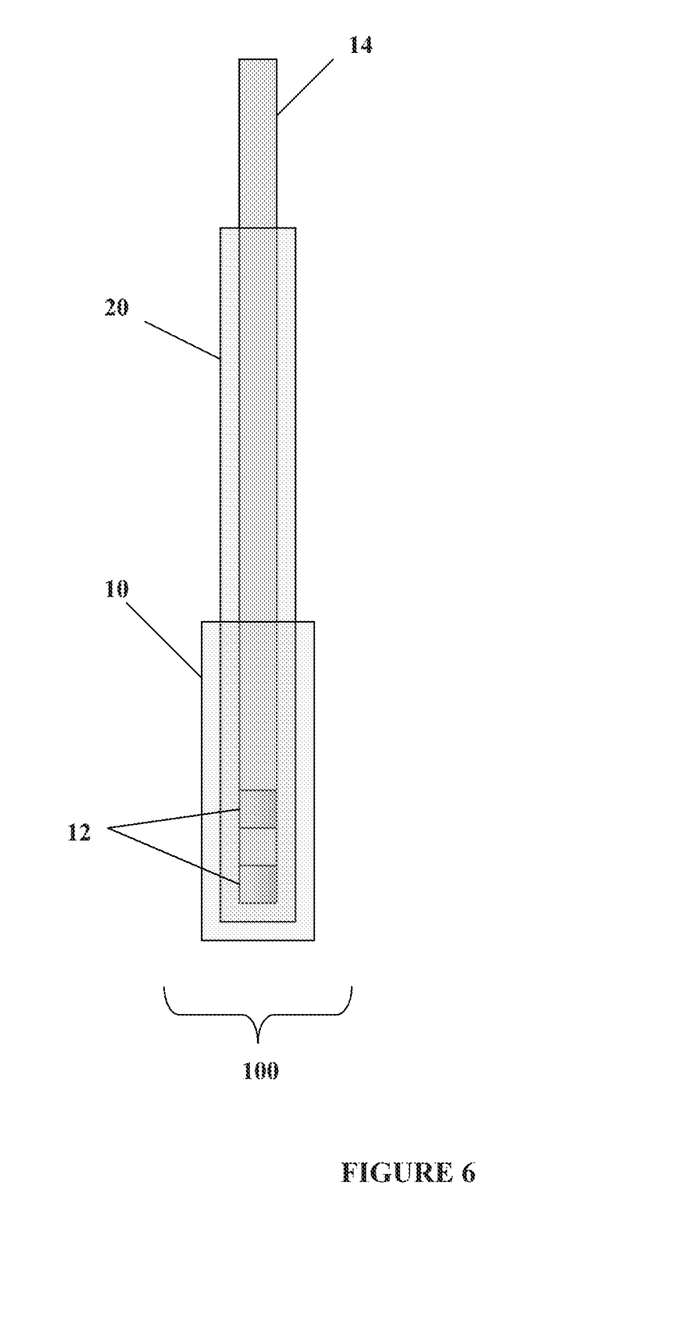
FIG. 6 is a schematic illustration of an example embodiment of the present invention comprising a magnetic needle insert with a sheath.

Referring now to FIG. 6, one embodiment of the present invention comprises magnetic biopsy apparatus 100 for collecting a biopsy sample of diseased cells from a subject with sheath 10. This embodiment preferably comprises cannulae 20 for penetrating a body of a subject having openings at the distal end and proximal end with the cross-sectional area in between the distal end and the proximal end substantially hollow for injecting superparamagnetic nanoparticles into a biopsy site of a potential through cannulae 20 which contacts the patient at the distal end of the apparatus 100. The superparamagnetic nanoparticles are labeled with a receptor for a specific target of interest of a diseased cell. The superparamagnetic nanoparticles do not attract each other in the absence of a magnetic field.

This embodiment further comprises rod 14 having a distal end and having at least one rare earth magnet 12 located at the distal end of rod 14, rod 14 capable of being inserted into and retracted from cannulae 20 with rare earth magnet 12 positionable partially outside of the proximal end of cannulae 20. Sheath 10 is preferably removable attached to rod 14 at the distal end and covers the portion of rod 14 where rare earth magnet 12 is located. Sheath 10 is preferably polyimide. In one embodiment the sheath 10 is removable attached to the rod 14. The sheath 10 is attached to the rod 14 when the rod 14 is inserted into the biopsy site. The superparamagnetic nano particles are attracted to the rare earth magnets 12 on the rod 14 and are localized on the sheath 10 which is positioned between the rare earth magnet 14 and the superparamagnetic nano particles.

According to one example the rod assembly provides that the length of the rod may be about 18.5 mm and be made of any biocompatible material for example grade 316 stainless steel. The rod can be held in a housing which can run the length of the rod or some portion thereof for example the housing can have a length of about 14 mm and cover the distal tip of the needle where the one or more rare-earth magnets are located. The rare-earth magnets can be of any type for example NdFeB. The housing or a portion thereof can be made from a biocompatible housing for example polyimide. The diameter of the rod assembly can be of any diameter. According to one embodiment the diameter of the rod assembly is about 0.108 mm.

A sheath can cover the housing at the distal end of the assembly where the rare-earth magnets of the rod are located. The sheath can cover only a portion of the rod and have for example a length of about 4.5 mm. The sheath can be removable attached to the housing or to the rod when the housing is not present.

The one or more rare-earth magnets located at the tip of the needle can be about 2 mm in length and 1 mm in diameter and separated from each other by about 2 mm according to one embodiment of the present invention. However, the size of the magnets is not limiting and other size magnets can create a similar magnetic force. For example the magnets can range in size from 0.5 to 4 mm. These dimensions and materials are for illustration purposes only and the embodiments of the present invention are not limited to these dimensions or materials.

EXAMPLE

Magnetic nanoparticles conjugated with antibodies for targeting specific eptitopes on an ALL surface, such as a cell surface receptor like CD34 are incubated with a population of cells to be assayed.

A magnetic needle surrounded by a sheath such as plastic according to one embodiment of the present invention is introduced into the cell and magnetic nanoparticle mixture. A plurality of rare-earth magnets at the distal end of the needle attracts magnetic nanoparticle bead complexes as well as nanoparticles uncomplexed to cells. The sheath may extend the length of the magnetic needle or may cover the needle at only a portion of the length. In one embodiment, magnets are about 2 mm in length and are spaced apart from each other at a distance of about 2 mm. Alternatively, a second sheath may surround this assembly for collection of nanoparticles and then removed with the nanoparticles subsequently placed in a solution for microscopic or other type measurements.

Magnetic nanoparticles incubated with target cells and forming a complex are attracted to the magnetic needle when the magnetic needle is put into close proximity to the magnetic nanoparticles. The magnetic nanoparticles through magnetic interaction with the rare-earth magnets locate to the plastic sheath at the distal end of the magnetic needle. Cells bound to the nanoparticle through the antibody are co-located to the needle with the nanoparticle via magnetic forces. The magnetic needle with the magnetic nanoparticles bound thereto are withdrawn from the assay environment. The nanoparticle/cell complexes are removed from the sheath for examination and analysis. For example, the nanoparticles/cell complexes removed from the sheath are analyzed with a SQUID sensor platform wherein the decaying remanence fields from the labeled cells after termination of the magnetic pulse is determined. See Flynn et al, in *Use of a SQUID Array To Detect T-cells With Magnetic Nanoparticles In Determining Transplant Rejection*, Journal of Magnetism and Magnetic Materials, 311, p 429 (2007).

In the present example CD34 Antibodies (Ab) that are specific to common ALL cells were conjugated to magnetic nanoparticles. One or more (for example, thousands of nanoparticles) may be attached to each cell thereby producing a large magnetic moment for attraction to the magnetic needle.

Figure 7:
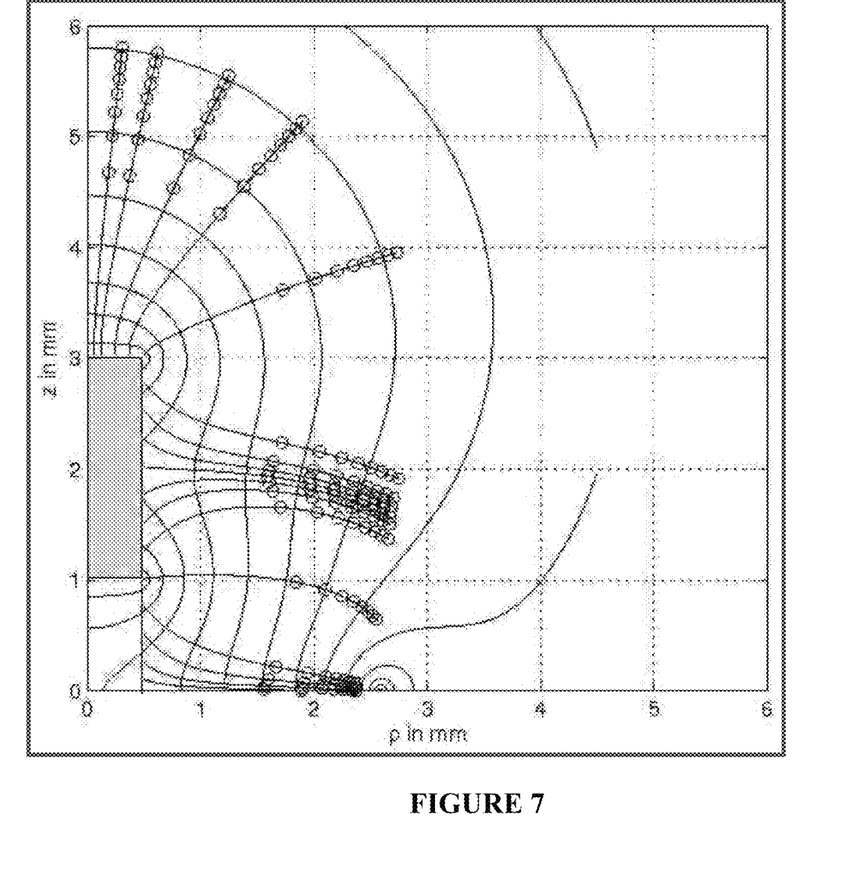
FIG. 7 is a schematic illustration of magnetic field contour lines for a rare-earth magnet.

Referring now to FIG. 7, a magnetic field contour line graph of the magnetic needle magnet (solid gray bar) and comparison data is illustrated: FIG. 7 contains the magnetic field gradient lines as calculated from the theory. The cells attracted by the magnet will tend to follow these lines. This has been confirmed by movies of particle movement.

Figure 8:
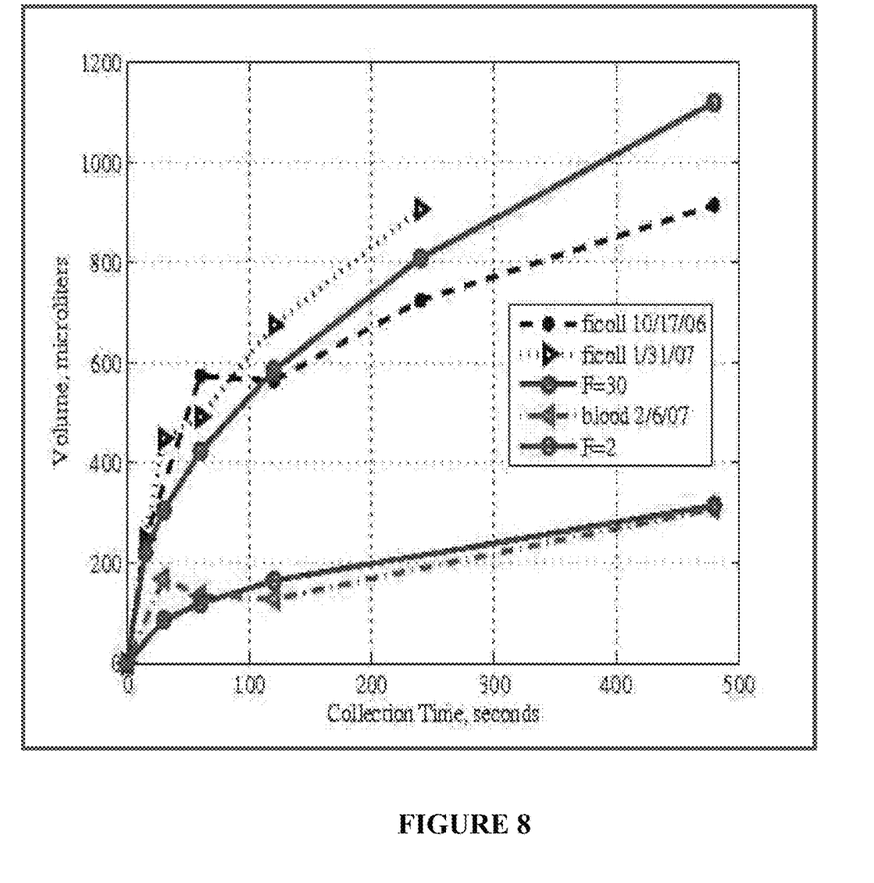
FIG. 8 is a schematic illustration of calculated collection times for various volumes of cells in suspension.

FIG. 8 illustrates calculated collection times for various volumes using several values of F, where F is for various field strengths of the magnets, from the equations above, representing different viscosities. Experimental data is shown using ficoll and blood to simulate very different viscous media.

Insertion of the magnetic rod in a vial containing recently extracted bone marrow diluted with blood produces a sheath having rings where the cells have been collected due to their complexation with the magnetic nanoparticles. These rings correspond to the regions of highest gradients as shown in the figure above.

In one embodiment of the present invention, the magnetic rod is a magnetic needle. It was unexpectedly observed that a ten fold increase in detection of target cells were observed with the magnetic needle over standard pathology techniques. A standard pathology cell count of 200 cells, noting how many of these were blast cells was conducted for both blood spiked with U937 cells and with fresh bone marrow from leukemia patients. Each case was diluted with blood by factors of two until reduced by 1024 in order to simulate a MRD situation where there will be much fewer blast cells.

This was done with the diluted preparation (after nanoparticles were added and incubated), followed by a one minute placement of the magnetic rod in the preparation with a subsequent removal of the collected cells. Table I and Table II give the results from blood spiked with U937 cells and for bone marrow samples from human leukemia cell donors diluted with normal bone marrow.

Table I illustrates the enhancement produced by the rod draws for the number of leukemia cells collected on the rod compared to those directly from the cell preparations results of Table II. A 10 fold increase in the sensitivity for MRD is seen in the rod draws for U937 cells while the number of cells in marrow is magnified by a factor of 5.4 over traditional pathology methods.

TABLE I

| Dilution | U937 Count | Needle Count | Needle Increase |
|---|---|---|---|
| 1/1 | 200/200 | 200/200 | NA |
| 1/2 | 127/200 | 144/200 | 1.13 |
| 1/4 | 71/200 | 94/200 | 1.32 |
| 1/8 | 44/200 | 78/200 | 1.77 |
| 1/16 | 28/200 | 49/200 | 1.75 |
| 1/32 | 13/200 | 32/200 | 2.46 |
| 1/64 | 6/200 | 21/200 | 3.50 |
| 1/128 | 4/200 | 12/200 | 3.00 |
| 1/256 | 2/200 | 7/200 | 3.50 |
| 1/512 | 1/200 | 8/200 | 8.00 |
| 1/1024 | 1/200 | 10/200 | 10.00 |

TABLE II

| Dilution | Marrow Count | Needle Count | Needle Increase |
|---|---|---|---|
| 1/1 | 192/200 | 194/200 | 1.01 |
| 1/2 | 169/200 | 189/200 | 1.12 |
| 1/4 | 148/200 | 151/200 | 1.02 |
| 1/8 | 123/200 | 139/200 | 1.13 |
| 1/16 | 96/200 | 119/200 | 1.24 |
| 1/32 | 79/200 | 103/200 | 1.30 |
| 1/64 | 64/200 | 99/200 | 1.55 |
| 1/128 | 54/200 | 82/200 | 1.52 |
| 1/256 | 39/200 | 79/200 | 2.03 |
| 1/512 | 26/200 | 69/200 | 2.65 |
| 1/1024 | 11/200 | 59/200 | 5.36 |

EXAMPLE

In production or collection of magnetic particles, it can be important to purify or concentrate samples by removing magnetic particles from a liquid suspension. A magnetic apparatus like those described herein can be used to facilitate rapid separation magnetic particles from organic or aqueous suspensions in either a batch or continuous flow format. Optical monitoring of solution turbidity can be used to monitor the separation process for optimal duration.

A magnetic apparatus for this example application can comprise permanent magnets arranged coaxially along a rod, and the configuration secured at the distal ends with a locking component comprised of a plate, a nut, or similar retaining structures. The locking mechanism can be configured to permit the adjustment of the position of the magnets along the axis. Adjusting the position of the magnets, and thus the spacing between magnets, further allows variation of the resulting magnetic field gradient. The size of the magnets used and the corresponding spacing between magnets can be selected based on (1) the volume being sampled and (2) the dimensions of the sample container, and (3) the properties of the particle suspension (including, as examples, one or more of particle size, concentration, colloidal stability of the suspension). The apparatus can comprise a magnet encased in a removable, disposable sheath that prevents direct contact between the apparatus and the sample. The properties of the sheath can be chosen for compatibility with the solution and the nanoparticles.

In a batch or semi-batch application, a magnetic needle can be comprised of a solid cylindrical apparatus that is submerged into a sample with a static volume. For batch operation, a magnetic needle apparatus can be submerged into solution until separation of particles from the solution occurs. Residence time of the magnetic needle in the suspension can be varied for desired separation of magnetic particles from solution. Following separation of the particles from solution, the sheathed needle and magnetically bound particles can be removed to a secondary container. Alternatively, the magnetic needle apparatus can remain fixed in position and the solution can be drained from the container by gravity or by pumping, leaving magnetic particles bound to the sheathed magnetic needle apparatus. In either embodiment, removal of the magnetic needle apparatus from the sheath, optionally combined with rinsing using an appropriate solvent releases the particles from the sheath. The particles can be re-suspended at the desired concentration in the solvent of choice. Additional separations using the needle can be performed for further purification or concentration.

In a continuous flow or semi-batch application, a magnetic needle can comprise annular, rather than solid, magnets. A tube can be inserted through axially aligned annuli to allow continuous, gravity driven or pumped flow of a suspension containing magnetic particles. The flow rate can be configured to determine the desired residence time of the particles in the magnetic needle apparatus. For semi-batch use, a volume of suspension containing magnetic particles can be introduced into annular space, with flow out of the space prevented by the use of a device such as a valve or stopper. Residence time of the suspension in the annular space can be selected for desired separation of magnetic particles from solution. Following separation of the particles from solution, opening of the valve or stopper apparatus allows the solution to be drained, leaving magnetic particles bound to the tubing within the magnetic needle apparatus. Removal of the tubing from the magnetic needle apparatus to a secondary container, optionally combined with rinsing using an appropriate solvent, releases the particles from the tubing. The particles can be re-suspended at the desired concentration in the solvent of choice. Additional separations using the needle can be performed for further purification or concentration.

The progress of the separation can be monitored with a probe that measures the optical density or turbidity of the solution. The probe can be used with an external device, such as a spectrometer, to monitor the solution in real time. The rate of change in the turbidity of solution can reflect the size of particles in solution, the presence of aggregates, and completion time of separation.

Figure 9:
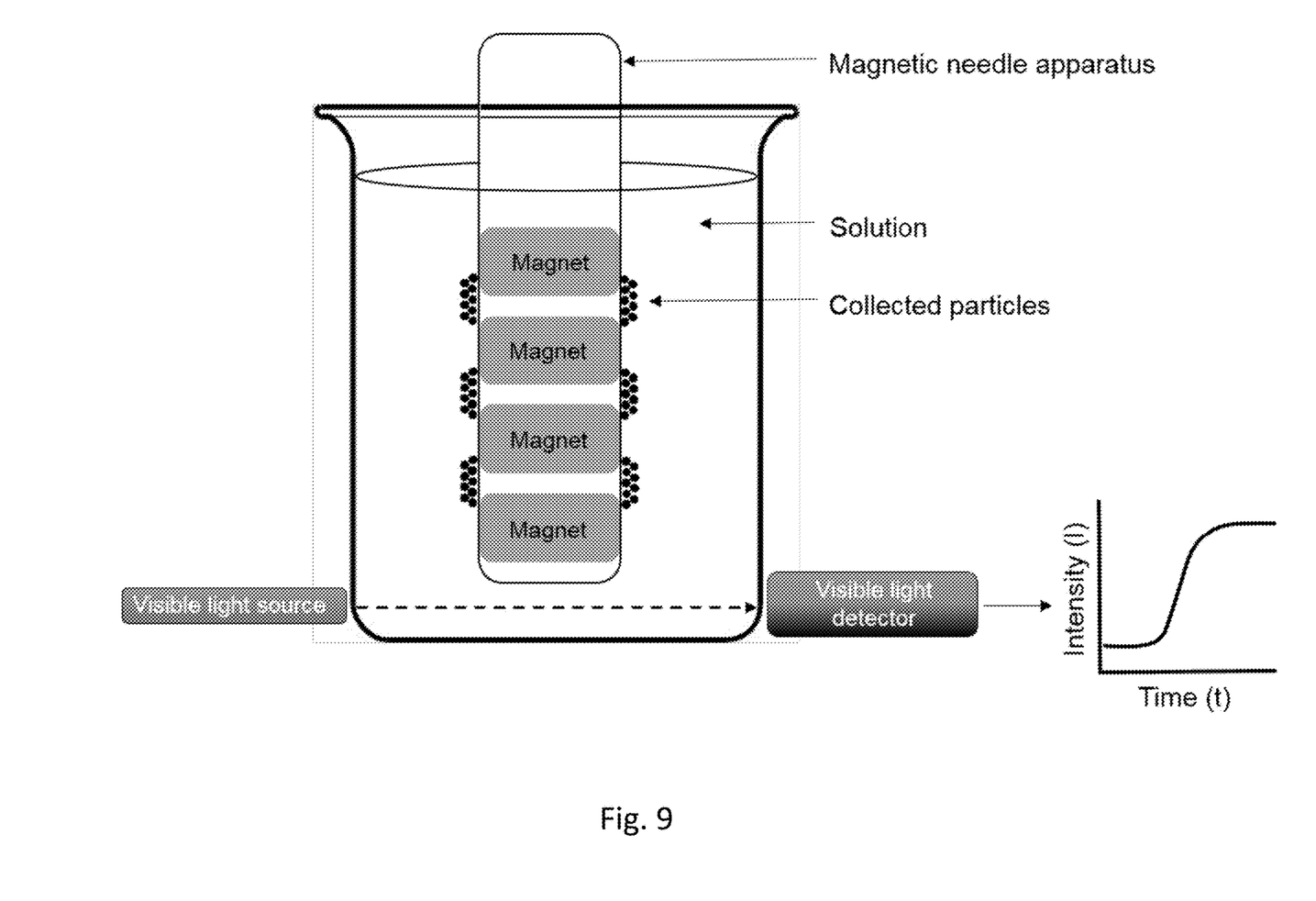
FIG. 9 is a schematic illustration of an example apparatus according to the present invention.

In an example embodiment, one can measure the time-dependent intensity of transmitted visible light through a colloidal suspension during the magnetic separation process. FIG. 9 is a schematic illustration of an example embodiment of the invention. A visible light source is externally coupled to the sample container. Light transmitted through the sample solution is measured by an externally coupled detector positioned at 180° to the light source. The visible light source can be comprised of a tungsten light source coupled to an optical fiber. The detector can be a spectrometer capable of measuring wavelengths between 400 and 600 nm. The position of the magnetic needle apparatus should be adjusted so as not to be in the path of the transmitted light. The intensity of transmitted light as a function of separation time can be recorded and plotted in real time.

The transmission of visible light through a suspension containing magnetic particles will be low with respect to a solution containing no magnetic particles. Thus, the intensity of transmitted light will increase over the course of a magnetic separation.

The intensity (I) as well as the rate of change of intensity (dI/dt) can be used to accomplish several objectives, such as those described below.

Monitor the progress of the separation: the intensity of transmitted light through a sample in which all particles have been removed from suspension will be maximum, and the rate of change of intensity=0. When I is maximum (or some other predetermined threshold), or dI/dt=0 (or some other predetermined threshold), or both, the separation process can be terminated.

Monitor the quality of the suspension based on dI/dt: In a given magnetic field gradient, a sample containing larger particles, or agglomerates of smaller particles will be removed from the suspension faster than smaller, non-agglomerating particles.

Monitor the relative concentration of a solution: If, over the progress of a separation, I remains relatively low and dI/dt=0, the needle apparatus might be saturated with magnetic particles. Additional separations might be required until I reaches a relative maximum. Alternatively, the size of the magnetic needle apparatus can be configured to increase the separation efficiency.

Optimize the configuration of the magnetic needle apparatus based on dI/dt: a sample containing larger particles will be removed from the suspension at lower magnetic gradients relative to a sample containing smaller particles. In a given configuration, this can result in a significantly different separation time or efficiency for large vs. small particles. For smaller particles, the magnetic needle apparatus can be configured to achieve higher magnetic gradients for optimal, more efficient separations as determined by monitoring dI/dt.

Although the present invention has been described in terms of various exemplary embodiments for purposes of illustration, those of ordinary skill in the art will appreciate that various modifications and improvement may be made to the described embodiments without departing from the scope of the invention.

What is claimed is:

1. An apparatus for the separation of magnetic particles from a suspension, comprising:
   (a) a magnetic needle configured to attract magnetic particles;
   (b) a light measurement system, comprising a light source configured to produce light at a first wavelength and a light detector configured to detect light at the first wavelength, configured to provide an optical path through the suspension from the light source to the light detector;
   (c) a control system, configured to control the apparatus responsive to the visible light measurement system.

2. An apparatus as in claim 1, wherein the magnetic needle comprises a plurality of bar magnets spaced apart along an axis.

3. An apparatus as in claim 1, wherein the light measuring system comprises a light source configured to provide light at one or more wavelengths in the visible range; a detector configured to detect light intensity at one or more of the wavelengths provided by the light source; wherein the light source and detector are mounted relative to each other such that an optical path from the light source to the detector passes through the suspension.

4. An apparatus as in claim 1, wherein the light measurement system is configured to provide an intensity signal representative of the light transmitted through the suspension as a function of time; and wherein the control system is configured to produce a status signal responsive to the intensity signal.

5. An apparatus as in claim 4, wherein the status signal indicates that the rate of change of the intensity signal with respect to time has reached a predetermined threshold.

6. An apparatus as in claim 5, wherein the status signal indicates that the rate of change of the intensity signal with respect to time has reached about zero.

7. An apparatus as in claim 4, wherein the status signal indicates that the intensity signal has reached a predetermined threshold.

8. An apparatus as in claim 7, wherein the status signal indicates that the intensity signal has reached about a maximum.

9. An apparatus as in claim 1, wherein the magnetic needle comprises a sheath that allows magnetic fields from the magnetic needle to affect magnetic particles in the suspension and prevents physical contact between the magnetic needle and the suspension.

10. A method of separating magnetic particles from a suspension, comprising:
    (a) providing an apparatus as in claim 1;
    (b) placing the suspension in optical communication with the light measurement system;
    (c) placing the magnetic needle in magnetic communication with the suspension;
    (d) removing the magnetic needle from contact with the suspension responsive to the control system.

11. A method as in claim 10, wherein the magnetic needle comprises a sheath that allows magnetic fields from the magnetic needle to affect magnetic particles in the suspension and prevents physical contact between the magnetic needle and the suspension.

12. A method as in claim 10, wherein the light measurement system is configured to provide an intensity signal representative of the light transmitted through the suspension as a function of time; and wherein the control system is configured to produce a status signal responsive to the intensity signal.

13. A method as in claim 12, wherein the magnetic needle is removed from contact with the suspension when the rate of change of the intensity signal as a function of time reaches a predetermined threshold.

14. A method as in claim 12, wherein the magnetic needle is removed from contact with the suspension when the intensity signal reaches a predetermined threshold.

15. An apparatus as in claim 1, wherein light is received at the detector after absorption and scattering along the optical path.

* * * * *